United States Patent
Omori et al.

(10) Patent No.: US 11,179,681 B2
(45) Date of Patent: Nov. 23, 2021

(54) SEPARATION MEMBRANE AND METHOD OF PRODUCING SEPARATION MEMBRANE

(71) Applicant: ZEON CORPORATION, Tokyo (JP)

(72) Inventors: Shiori Omori, Tokyo (JP); Takahiro Suzuki, Tokyo (JP); Takashi Sasanuma, Tokyo (JP); Hideaki Miki, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 229 days.

(21) Appl. No.: 16/491,723

(22) PCT Filed: Mar. 27, 2018

(86) PCT No.: PCT/JP2018/012486
§ 371 (c)(1),
(2) Date: Sep. 6, 2019

(87) PCT Pub. No.: WO2018/181349
PCT Pub. Date: Oct. 4, 2018

(65) Prior Publication Data
US 2020/0078743 A1    Mar. 12, 2020

(30) Foreign Application Priority Data

Mar. 28, 2017 (JP) .............................. JP2017-063339

(51) Int. Cl.
*B01D 69/10* (2006.01)
*B01D 69/12* (2006.01)
(Continued)

(52) U.S. Cl.
CPC ............ *B01D 69/10* (2013.01); *B01D 69/12* (2013.01); *B01D 71/028* (2013.01); *C01B 39/40* (2013.01); *C07C 9/18* (2013.01)

(58) Field of Classification Search
CPC .... B01D 71/028; B01D 69/10; B01D 53/228; B01D 69/12; B01D 69/02; B01D 61/362; B01D 2256/24; B01D 71/02
See application file for complete search history.

(56) References Cited

U.S. PATENT DOCUMENTS 6,818,333 B2 * 11/2004 Chau ................... B01D 53/228
                                                  210/500.21
7,049,259 B1 *  5/2006 Deckman ........... B01D 67/0046
                                                          502/4
(Continued)

FOREIGN PATENT DOCUMENTS

CN         102348494 A     2/2012
CN         104888618 A     9/2015
(Continued)

OTHER PUBLICATIONS

Oct. 1, 2019, International Preliminary Report on Patentability issued in the International Patent Application No. PCT/JP2018/012486.
(Continued)

*Primary Examiner* — Ana M Fortuna
(74) *Attorney, Agent, or Firm* — Kenja IP Law PC

(57) ABSTRACT

Provided is a separation membrane that is suitable for use in separating one or more hydrocarbons from a hydrocarbon mixture. More specifically, the separation membrane includes a porous support for which acid content is not substantially detected by ammonia temperature programmed desorption in a temperature range of higher than 450° C. and not higher than 600° C. and a porous separation layer containing a zeolite that is disposed on the porous support.

5 Claims, 1 Drawing Sheet

(51) Int. Cl.
 *B01D 71/02* (2006.01)
 *C01B 39/40* (2006.01)
 *C07C 9/18* (2006.01)

(56) References Cited

U.S. PATENT DOCUMENTS

| | | | | |
|---|---|---|---|---|
| 8,153,099 | B2* | 4/2012 | Yoon | B01D 67/0051 |
| | | | | 423/707 |
| 2003/0084786 | A1* | 5/2003 | Chau | B01D 67/0051 |
| | | | | 95/45 |
| 2009/0000475 | A1* | 1/2009 | Fekety | B01J 35/065 |
| | | | | 95/105 |
| 2009/0264550 | A1* | 10/2009 | Rayner | B01D 67/0027 |
| | | | | 521/189 |
| 2012/0000358 | A1* | 1/2012 | Kawai | B01D 67/0051 |
| | | | | 95/46 |
| 2014/0360938 | A1* | 12/2014 | Hayashi | B01D 69/125 |
| | | | | 210/638 |
| 2020/0114307 | A1* | 4/2020 | Tanaka | B01D 67/0051 |
| 2021/0163380 | A1* | 6/2021 | Suzuki | C07C 11/20 |

FOREIGN PATENT DOCUMENTS

| | | | | |
|---|---|---|---|---|
| JP | H11137981 | A | 5/1999 | |
| JP | 2002-348579 | * | 12/2002 | B01D 71/02 |
| JP | 2002348579 | A | 12/2002 | |
| JP | 2015160186 | A | 9/2015 | |

OTHER PUBLICATIONS

May 15, 2018, International Search Report issued in the International Patent Application No. PCT/JP2018/012486.

T. Finke et al., Numerical modelling of the adsorption and thermal desorption of NH3 on ZrO2, Thermochimica Acta, 2008, pp. 32-39, vol. 473.

* cited by examiner

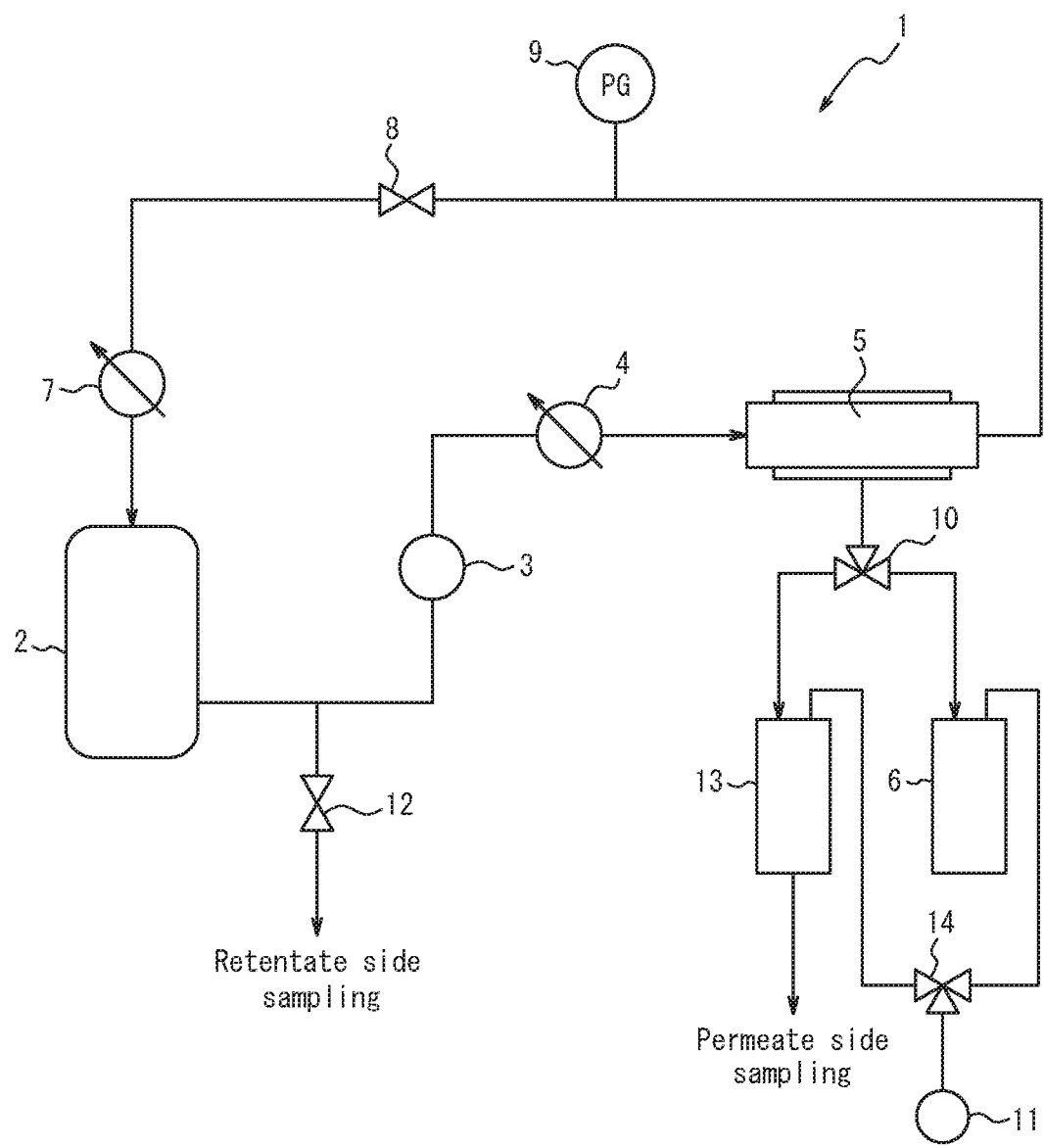

SEPARATION MEMBRANE AND METHOD OF PRODUCING SEPARATION MEMBRANE

TECHNICAL FIELD

The present disclosure relates to a separation membrane and a method of producing a separation membrane, and, in particular, relates to a separation membrane that is suitable for use in separating one or more hydrocarbons from a hydrocarbon mixture and to a method of producing this separation membrane.

BACKGROUND

Membrane separation is conventionally used as a low-energy method for separating a branched hydrocarbon from a hydrocarbon mixture containing linear and branched hydrocarbons of equivalent carbon number. Zeolite membranes that are obtained by forming a zeolite in a film-like form on a support are widely used as separation membranes.

In one specific example, Patent Literature (PTL) 1 discloses the separation of isobutene from a mixture of 1-butene and isobutene using a composite membrane including a porous substrate and a porous separation layer that contains an MFI-type zeolite on the surface of the porous substrate. In PTL 1, a zeolite membrane is obtained by forming a porous separation layer containing a zeolite that includes aluminum and silicon in a specific ratio on a support that is a ceramic substrate such as mullite.

CITATION LIST

Patent Literature

PTL 1: JP 2015-160186 A

SUMMARY

Technical Problem

However, studies carried out by the inventors in relation to membrane separation of hydrocarbon mixtures using the conventional zeolite membrane described above have revealed that separation performance may decrease with increasing length of use when the conventional zeolite membrane described above is used in separation of a hydrocarbon mixture.

Accordingly, an objective of the present disclosure is to provide a separation membrane that can maintain excellent separation performance over a long period when used in membrane separation of a hydrocarbon mixture containing a linear hydrocarbon and a branched hydrocarbon and/or cyclic hydrocarbon of equivalent carbon number to the linear hydrocarbon, and also to provide a method of producing this separation membrane.

Solution to Problem

The inventors conducted diligent investigation to achieve the objective set forth above. As a result, the inventors made a new finding that a separation membrane formed using a porous support that satisfies a specific condition can display excellent separation performance over a long period by maintaining high levels of separation selectivity and separation efficiency. In this manner, the inventors completed the present disclosure.

Specifically, the present disclosure aims to advantageously solve the problem set forth above by disclosing a separation membrane that is for use in membrane separation of a hydrocarbon mixture containing a linear hydrocarbon and either or both of a branched hydrocarbon and a cyclic hydrocarbon of equivalent carbon number to the linear hydrocarbon, and that comprises: a porous support for which acid content is not substantially detected by ammonia temperature programmed desorption in a temperature range of higher than 450° C. and not higher than 600° C.; and a porous separation layer containing a zeolite that is disposed on the porous support.

A separation membrane in which a porous separation layer containing a zeolite is disposed on a porous support for which acid content is not substantially detected by ammonia temperature programmed desorption in a temperature range of higher than 450° C. and not higher than 600° C. (i.e., that does not include so-called "strong acid sites") as set forth above can maintain excellent separation performance over a long period when used in membrane separation of a hydrocarbon mixture containing a linear hydrocarbon and a branched hydrocarbon and/or cyclic hydrocarbon of equivalent carbon number to the linear hydrocarbon.

The term "zeolite" as used in the present specification refers to a Si-containing compound having a porous structure.

Moreover, the phrase "acid content is not substantially detected by ammonia temperature programmed desorption" as used in the present specification means that the amount of ammonia desorbed from a measurement target in a temperature range of higher than 450° C. and not higher than 600° C. is less than the detection limit, and, more specifically, is less than 0.4 μmol/g.

In the presently disclosed separation membrane, the porous support is preferably shirasu porous glass. By using shirasu porous glass as the porous support, the porous membrane can maintain even better separation performance over a long period when used in membrane separation.

The presently disclosed separation membrane preferably further comprises boron. Through inclusion of boron, the separation membrane can further improve separation selectivity when used in membrane separation.

Moreover, the present disclosure aims to advantageously solve the problem set forth above by disclosing a method of producing a separation membrane for use in membrane separation of a hydrocarbon mixture containing a linear hydrocarbon and either or both of a branched hydrocarbon and a cyclic hydrocarbon of equivalent carbon number to the linear hydrocarbon, the method comprising a step (A) of forming a porous separation layer containing a zeolite on a porous support for which acid content is not substantially detected by ammonia temperature programmed desorption in a temperature range of higher than 450° C. and not higher than 600° C.

By forming a porous separation layer containing a zeolite on a porous support for which acid content is not substantially detected by ammonia temperature programmed desorption in a temperature range of higher than 450° C. and not higher than 600° C. (i.e., that does not include so-called "strong acid sites") as set forth above, it is possible to favorably form a separation membrane that can maintain excellent separation performance over a long period when used in membrane separation of a hydrocarbon mixture containing a linear hydrocarbon, a branched hydrocarbon and/or a cyclic hydrocarbon.

In the presently disclosed method of producing a separation membrane, the porous support is preferably shirasu porous glass. By using shirasu porous glass as the porous support, a separation membrane having a porous separation layer containing a zeolite disposed on the porous support can easily be formed.

In the presently disclosed method of producing a separation membrane, the step (A) preferably further includes immersing the porous support in an aqueous sol containing a silica source, a structure directing agent, and a boron source after one or more silicalite seed crystals have been adhered to the porous support. Immersion of the porous support in an aqueous sol containing a silica source, a structure directing agent, and a boron source after silicalite seed crystals have been adhered thereto enables good, efficient formation of the porous separation layer.

In the presently disclosed method of producing a separation membrane, a ratio of an amount of the silica source and an amount of the boron source contained in the aqueous sol, as a molar ratio, is preferably within a range of 1:0.01 to 1:1. The use of an aqueous sol that contains a silica source and a boron source in the proportions set forth above enables good, efficient formation of a porous separation layer containing a boron-containing zeolite.

Advantageous Effect

According to the present disclosure, it is possible to provide a separation membrane that can maintain excellent separation performance over a long period when used in membrane separation of a hydrocarbon mixture containing a linear hydrocarbon and a branched hydrocarbon and/or cyclic hydrocarbon of equivalent carbon number to the linear hydrocarbon, and also to provide a method of producing this separation membrane.

BRIEF DESCRIPTION OF THE DRAWING

In the accompanying drawing,

FIG. 1 illustrates an overview of configuration of a test apparatus used in the examples.

DETAILED DESCRIPTION

The following provides a detailed description of embodiments of the present disclosure.

The presently disclosed separation membrane can be used in membrane separation of a hydrocarbon mixture containing a linear hydrocarbon and a branched hydrocarbon and/or cyclic hydrocarbon of equivalent carbon number to the linear hydrocarbon. Moreover, the presently disclosed separation membrane can be produced by the presently disclosed method of producing a separation membrane, for example.

(Separation Membrane)

The presently disclosed separation membrane that is used in membrane separation of a hydrocarbon mixture is a separation membrane that includes a porous support for which acid content is not substantially detected by ammonia temperature programmed desorption in a temperature range of higher than 450° C. and not higher than 600° C. and a porous separation layer containing a zeolite that is disposed on the porous support. As a result of the presently disclosed separation membrane including a porous separation layer containing a zeolite that is disposed on a porous support for which acid content is not substantially detected by ammonia temperature programmed desorption in a temperature range of higher than 450° C. and not higher than 600° C. (i.e., that does not include so-called "strong acid sites"), the presently disclosed separation membrane can maintain excellent separation performance over a long period when used in membrane separation of a hydrocarbon mixture containing a linear hydrocarbon and a branched hydrocarbon and/or cyclic hydrocarbon of equivalent carbon number to the linear hydrocarbon.

<Hydrocarbon Mixture>

The hydrocarbon mixture that is membrane separated using the presently disclosed separation membrane is a mixture that contains a linear hydrocarbon and a branched hydrocarbon and/or cyclic hydrocarbon of equivalent carbon number to the linear hydrocarbon. Moreover, the hydrocarbon mixture that is membrane separated using the presently disclosed separation membrane is preferably a mixture that contains, as main components, a linear hydrocarbon having a carbon number of 4 and a branched hydrocarbon having a carbon number of 4 and/or a cyclic hydrocarbon having a carbon number of 4, or a mixture that contains, as main components, a linear hydrocarbon having a carbon number of 5 and a branched hydrocarbon having a carbon number of 5 and/or a cyclic hydrocarbon having a carbon number of 5, and is more preferably a mixture that contains, as main components, a linear hydrocarbon having a carbon number of 5 and a branched hydrocarbon having a carbon number of 5 and/or a cyclic hydrocarbon having a carbon number of 5. The presently disclosed separation membrane enables efficient separation of a hydrocarbon mixture containing, as main components, a linear hydrocarbon having a carbon number of 4 or 5 and a branched hydrocarbon and/or cyclic hydrocarbon of equivalent carbon number to the linear hydrocarbon. In particular, the presently disclosed separation membrane enables efficient separation of a hydrocarbon mixture containing, as main components, a linear hydrocarbon having a carbon number of 5 and a branched hydrocarbon having a carbon number of 5 and/or a cyclic hydrocarbon having a carbon number of 5.

The phrase "containing, as main components, a linear hydrocarbon and a branched hydrocarbon and/or cyclic hydrocarbon" as used in the present disclosure means that the hydrocarbon mixture comprises 50 mol % or more, in total, of the linear hydrocarbon and the branched hydrocarbon and/or cyclic hydrocarbon.

The mixture containing, as main components, a linear hydrocarbon having a carbon number of 4 and a branched hydrocarbon and/or cyclic hydrocarbon having a carbon number of 4 may, for example, be a mixture containing a linear hydrocarbon having a carbon number of 4 such as n-butane, 1-butene, 2-butene, or butadiene, and a branched hydrocarbon having a carbon number of 4 such as isobutane or isobutene and/or a cyclic hydrocarbon having a carbon number of 4 such as cyclobutane or cyclobutene. Specifically, the mixture containing, as main components, a linear hydrocarbon having a carbon number of 4 and a branched hydrocarbon and/or cyclic hydrocarbon having a carbon number of 4 may, for example, be a C4 fraction obtained as a by-product in thermal cracking of naphtha to produce ethylene or a fraction that remains after recovering at least some butadiene from this C4 fraction.

The mixture containing, as main components, a linear hydrocarbon having a carbon number of 5 and a branched hydrocarbon and/or cyclic hydrocarbon having a carbon number of 5 may, for example, be a mixture containing a linear hydrocarbon having a carbon number of 5 such as n-pentane, 1-pentene, 2-pentene, or 1,3-pentadiene, and a branched hydrocarbon having a carbon number of 5 such as isopentane, 2-methyl-1-butene, 2-methyl-2-butene, 3-methyl-1-butene, or isoprene and/or a cyclic hydrocarbon having a carbon number of 5 such as cyclopentane or cyclopentene. Specifically, the mixture containing, as main components, a linear hydrocarbon having a carbon number of 5 and a branched hydrocarbon and/or cyclic hydrocarbon having a carbon number of 5 may, for example, be a C5 fraction obtained as a by-product in thermal cracking of naphtha to produce ethylene or a fraction that remains after recovering at least some isoprene from this C5 fraction.

<Porous Support>

The porous support is a porous body having pores therein. A porous support for which acid content is not substantially detected by temperature programmed desorption in a temperature range of higher than 450° C. and not higher than 600° C. is used as the porous support of the presently disclosed separation membrane. The porous support may, for example, be a porous body made from glass such as shirasu porous glass; ceramic such as silicon dioxide (silica) or titania; or metal such as stainless steel, and is preferably shirasu porous glass.

The porous support may have any shape such as a flat film shape, a flat plate shape, a tube shape, or a honeycomb shape without any specific limitations.

The average pore diameter of the porous support is preferably 0.1 μm or more, more preferably 0.5 μm or more, even more preferably 0.7 μm or more, and particularly preferably 1.0 μm or more, and is preferably 10 μm or less, more preferably 5.0 μm or less, even more preferably 3.0 μm or less, and particularly preferably 2.0 μm or less. With regards to the pore diameter distribution of the porous support, a value d10/d90 obtained by dividing a particle diameter d10 at which cumulative pore volume is 10% of total pore volume and a particle diameter d90 at which cumulative pore volume is 90% of total pore volume is preferably 10 or less, more preferably 5 or less, and even more preferably 2 or less.

The "average pore diameter of a porous support" and "pore diameter distribution of a porous support" referred to in the present disclosure can be measured by mercury intrusion porosimetry using a mercury porosimeter.

<Porous Separation Layer>

The porous separation layer is a porous body that includes pores and that is provided in order to separate a linear hydrocarbon and a branched hydrocarbon and/or cyclic hydrocarbon of equivalent carbon number to the linear hydrocarbon. A porous separation layer containing a zeolite is used as the porous separation layer of the presently disclosed separation membrane. The "zeolite" preferably has an MFI-type porous structure and includes Si in the skeletal structure thereof. Therefore, the term "zeolite" as used in the present specification is inclusive of silicalite that is composed substantially of only Si and O and has an MFI-type porous structure in addition to zeolites in a narrow sense defined generally as aluminosilicates. The porous separation layer containing a zeolite may be formed by, for example, immersing a porous support having one or more zeolite seed crystals adhered thereto in an aqueous sol containing a silica source and a structure directing agent, and optionally further containing a boron source, and forming the porous separation layer by hydrothermal synthesis.

The zeolite forming the porous separation layer is preferably silicalite that is composed substantially of only Si and O. By forming the porous separation layer from silicalite, the separation membrane can maintain excellent separation performance over an even longer period when used in membrane separation.

[Layer Thickness]

The thickness of the porous separation layer is preferably 1 μm or more, more preferably 2 μm or more, and even more preferably 5 μm or more, and is preferably 90 μm or less, and more preferably 70 μm or less. Setting the thickness of the porous separation layer as not less than any of the lower limits set forth above can inhibit the formation of pinholes and can raise the separation factor of the separation membrane, which further improves separation efficiency with respect to a linear hydrocarbon and a branched hydrocarbon and/or cyclic hydrocarbon of equivalent carbon number to the linear hydrocarbon. Moreover, setting the thickness of the porous separation layer as not more than any of the upper limits set forth above can suppress a decrease in permeation flux of the separation membrane, and thereby further improve separation efficiency with respect to a linear hydrocarbon and a branched hydrocarbon and/or cyclic hydrocarbon of equivalent carbon number to the linear hydrocarbon.

The "thickness of a porous separation layer" can be measured using a scanning electron microscope (SEM). Moreover, the thickness of the porous separation layer can be controlled by adjusting the average particle diameter of zeolite seed crystals used to form the porous separation layer, the zeolite synthesis conditions (for example, temperature and time), and so forth.

<Properties of Separation Membrane>

The separation membrane preferably contains boron. The inclusion of boron in the separation membrane can further improve separation selectivity when the separation membrane is used in membrane separation. In the separation membrane, boron may be contained in the porous separation layer and/or the porous support, but is preferably contained in at least the porous separation layer. As described above, in a case in which boron is contained in the porous separation layer, the porous separation layer containing boron can be obtained by compounding a boron source in the aqueous sol used in formation of the porous separation layer, and then carrying out hydrothermal synthesis by a standard method.

(Method of Producing Separation Membrane)

The presently disclosed separation membrane including the porous separation layer having the properties set forth above can easily be produced using the presently disclosed method of producing a separation membrane, for example.

The presently disclosed method of producing a separation membrane includes a step (A) of forming a porous separation layer containing a zeolite on a specific porous support, and may optionally further include a step of preparing zeolite seed crystals (seed crystal preparation step) and a step of adhering the zeolite seed crystals that have been prepared in the seed crystal preparation step to the porous support (seed crystal adhesion step). These steps are described below in detail. It should be noted that compounds and the like given as examples of components that can be used in the various steps may be one type used individually or a plurality of types used as a mixture. In a case in which a plurality of types are used, the total quantity thereof preferably satisfies quantity ratios described in relation thereto.

In the presently disclosed method of producing a separation membrane, the porous support having zeolite seed crystals adhered thereto may be obtained by synthesizing a zeolite that then serves as seed crystals on a porous support that does not already have zeolite seed crystals adhered thereto. However, from a viewpoint of forming a porous separation layer having good properties and obtaining a separation membrane having excellent separation efficiency, the porous support having zeolite seed crystals adhered thereto is preferably obtained by adhering zeolite seed crystals that have been prepared in advance onto the porous support. In other words, it is preferable that the seed crystal preparation step and the seed crystal adhesion step are implemented in the presently disclosed method of producing a separation membrane.

<Seed Crystal Preparation Step>

The seed crystal preparation step may be a step in which zeolite seed crystals are produced by a known method of producing zeolite seed crystals, but is not specifically limited thereto.

Specifically, the seed crystal preparation step may involve, for example, preparing zeolite seed crystals by heating an aqueous sol for seed crystals obtained through mixing of a silica source, a structure directing agent, and water, producing coarse zeolite crystals by hydrothermal synthesis, and then optionally drying and grinding the coarse crystals that are obtained.

[Aqueous Sol for Seed Crystals]

The aqueous sol for seed crystals may be any aqueous sol from which zeolite crystals can be prepared by hydrothermal synthesis.

Examples of silica sources that can be used in the aqueous sol for seed crystals include, but are not specifically limited to, colloidal silica, wet silica, amorphous silica, fumed silica, sodium silicate, silica sol, silica gel, kaolinite, diatomite, white carbon black, tetrabutoxysilane, tetrabutyl orthosilicate, and tetraethoxysilane. One of these silica sources may be used individually, or a plurality of these silica sources may be used in combination. Of these silica sources, tetraethoxysilane and colloidal silica are preferable, and tetraethoxysilane is more preferable.

Examples of structure directing agents that can be used include, but are not specifically limited to, alcohols and quaternary ammonium salts such as tetraethylammonium hydroxide, tetrapropylammonium hydroxide, and tetrapropylammonium bromide. One of these structure directing agents may be used individually, or a plurality of these structure directing agents may be used in combination. Of these structure directing agents, tetraethylammonium hydroxide, tetrapropylammonium hydroxide, and tetrapropylammonium bromide are preferable. Although the mixing ratio of the structure directing agent is not specifically limited, a molar ratio of the silica source and the structure directing agent (silica source:structure directing agent) is preferably within a range of 1:0.01 to 1:2.0, more preferably within a range of 1:0.1 to 1:1.0, and even more preferably within a range of 1:0.15 to 1:0.8.

Moreover, although the mixing ratio of water in the aqueous sol for seed crystals is not specifically limited, a molar ratio of the silica source and water (silica source: water) is preferably within a range of 1:3 to 1:100, and more preferably within a range of 1:5 to 1:50.

[Hydrothermal Synthesis of Coarse Crystals]

The heating temperature when the aqueous sol for seed crystals is heated to obtain coarse crystals by hydrothermal synthesis is preferably not lower than 100° C. and not higher than 200° C., and more preferably not lower than 130° C. and not higher than 150° C. The heating time is preferably not less than 10 hours and not more than 50 hours, and more preferably not less than 20 hours and not more than 50 hours.

The hydrothermal synthesis is typically carried out by adding the aqueous sol for seed crystals into a pressure-resistant vessel and then heating the pressure-resistant vessel under the conditions set forth above. Examples of pressure-resistant vessels that can be used include, but are not specifically limited to, a stainless steel pressure-resistant vessel including a fluororesin inner cylinder, a nickel metal pressure-resistant vessel, and a fluororesin pressure-resistant vessel. Examples of methods by which the pressure-resistant vessel can be heated include a method in which the pressure-resistant vessel is heated in a hot-air dryer and a method in which the pressure-resistant vessel is heated by a directly attached heater.

The coarse crystals obtained through heating of the aqueous sol for seed crystals can be collected by a known solid-liquid separation technique such as centrifugal separation. The coarse crystals that are collected may be used as zeolite seed crystals as collected, or may be used as zeolite seed crystals after drying and grinding.

[Drying and Grinding of Coarse Crystals]

The temperature at which the collected coarse crystals are dried is preferably not lower than 70° C. and not higher than 100° C., but is not specifically limited to this range. Moreover, no specific limitations are placed on the grinding method and conditions in grinding of the coarse crystals, and a method and conditions that enable a desired average particle diameter to be obtained may be adopted.

<Seed Crystal Adhesion Step>

In the seed crystal adhesion step, the zeolite seed crystals may be adhered to (mounted on) the porous support by a known technique such as coating, rubbing, filtration, or impregnation. Specifically, zeolite seed crystals may be adhered to a porous support by applying, onto the porous support, a dispersion liquid obtained by dispersing the zeolite seed crystals in water, and then drying the dispersion liquid that has been applied. Alternatively, zeolite seed crystals may be adhered to a porous support in the seed crystal adhesion step by rubbing zeolite seed crystals onto a porous support that has been wetted in advance through immersion in ultrapure water for 1 minute to 60 minutes. Moreover, zeolite seed crystals may be adhered to a porous support by using the porous support to filter a dispersion liquid obtained by dispersing the zeolite seed crystals in water. Furthermore, zeolite seed crystals may be adhered to a porous support by impregnating the porous support with a dispersion liquid obtained by dispersing the zeolite seed crystals in water.

From a viewpoint of adhering zeolite seed crystals to a porous support in a high density, zeolite seed crystals are preferably adhered to a porous support in the seed crystal adhesion step by rubbing the zeolite seed crystals onto a pre-wetted porous support.

The average particle diameter of the zeolite seed crystals is preferably 50 nm or more, and is preferably 700 nm or less, more preferably 600 nm or less, and particularly preferably 550 nm or less. When the average particle diameter of the zeolite seed crystals is within any of the ranges set forth above, a porous separation layer having good properties can be formed, separation selectivity can be further improved, and separation efficiency can be maintained over an even longer period.

The "average particle diameter of zeolite seed crystals" referred to in the present disclosure can be determined by calculating the number average of particle diameters of 20 zeolite seed crystals measured using a scanning electron microscope (SEM).

The porous support to which the zeolite seed crystals are adhered is preferably a porous support that enables a ratio of the average particle diameter of the zeolite seed crystals relative to the average pore diameter of the porous support of not less than 0.01 and not more than 0.70. In other words, the zeolite seed crystals used in the presently disclosed method of producing a separation membrane preferably have a specific average particle diameter that is smaller than the average pore diameter of the porous support. Specifically, the porous support may be any of the porous supports described in the preceding "<Porous support>" section. Moreover, the ratio of the average particle diameter of the zeolite seed crystals relative to the average pore diameter of the porous support is more preferably 0.04 or more, and is more preferably 0.60 or less, even more preferably 0.50 or less, and particularly preferably 0.40 or less. Formation efficiency of the porous separation layer can be improved by setting the ratio of the average particle diameter of the zeolite seed crystals and the average pore diameter of the porous support within any of the ranges set forth above. Although the reason for this is not clear, it is presumed that when zeolite seed crystals having the average particle diameter set forth above and a porous support having the average pore diameter set forth above are used, the zeolite seed crystals enter the pores of the porous support, which suitably restricts the direction of zeolite growth and thereby facilitates formation of a porous separation layer having the properties set forth above.

The adhered zeolite seed crystals can be fixed to the porous support by removing moisture contained in the porous support by drying. The temperature during this drying is not specifically limited but is preferably 50° C. or higher, and more preferably 70° C. or higher, and is preferably 150° C. or lower, and more preferably 100° C. or lower.

<Step (A)>

The step (A) is a separation membrane formation step. In the step (A), the porous support having the zeolite seed crystals adhered thereto is immersed in an aqueous sol containing a silica source and a structure directing agent, and a zeolite is synthesized by hydrothermal synthesis to form a porous separation layer on the porous support. A separation membrane obtained by forming the porous separation layer on the porous support in the step (A) may optionally be subjected to boil washing and/or firing treatment.

[Aqueous Sol]

The aqueous sol used in formation of the porous separation layer can be prepared by mixing a silica source, a structure directing agent, water, and, optionally, a boron source. Note that the aqueous sol used to form the porous separation layer preferably does not contain Al components.

Examples of silica sources that can be used include, but are not specifically limited to, colloidal silica, wet silica, amorphous silica, fumed silica, sodium silicate, silica sol, silica gel, kaolinite, diatomite, white carbon black, tetrabutoxysilane, tetrabutyl orthosilicate, and tetraethoxysilane. One of these silica sources may be used individually, or a plurality of these silica sources may be used in combination. Of these silica sources, tetraethoxysilane and colloidal silica are preferable, and tetraethoxysilane is more preferable.

Examples of structure directing agents that can be used include, but are not specifically limited to, crown ethers, alcohols, and quaternary ammonium salts such as tetraethylammonium hydroxide, tetrapropylammonium hydroxide, and tetrapropylammonium bromide. One of these structure directing agents may be used individually, or a plurality of these structure directing agents may be used in combination. Of these structure directing agents, tetraethyl ammonium hydroxide, tetrapropylammonium hydroxide, and tetrapropylammonium bromide are preferable, and the combined use of tetrapropylammonium hydroxide and tetrapropylammonium bromide is more preferable.

Although the mixing ratio of the structure directing agent in the aqueous sol is not specifically limited, a molar ratio of the silica source and the structure directing agent (silica source:structure directing agent) is preferably within a range of 1:0.01 to 1:2.0, more preferably within a range of 1:0.1 to 1:1.0, and even more preferably within a range of 1:0.15 to 1:0.8.

The boron source that is optionally compounded in the aqueous sol may be boric acid, for example, but is not specifically limited thereto. Note that boron contained in the porous separation layer of the separation membrane obtained through this step is not thought to be limited to the boron source that is optionally compounded in the aqueous sol. In a case in which the porous support itself is a material that contains boron, it is thought that this boron may become part of a source of an element that may be contained in the porous separation layer of the obtained separation membrane. More specifically, it is presumed that boron contained in the porous support elutes during the subsequently described hydrothermal synthesis of a zeolite and becomes incorporated into the porous separation layer containing the zeolite.

Although the mixing ratio of the boron source in the aqueous sol is not specifically limited, a molar ratio of the silica source and the boron source (silica source:boron source) is preferably within a range of 1:0.01 to 1:1, and more preferably within a range of 1:0.02 to 1:0.5. In a case in which the aqueous sol contains a plurality of boron sources, the mixing ratio described above may be taken to be the ratio of the total molar amount of the plurality of boron sources and the molar amount of the silica source.

Moreover, although the mixing ratio of water in the aqueous sol is not specifically limited, a molar ratio of the silica source and water (silica source:water) is preferably within a range of 1:100 to 1:1,000, and more preferably within a range of 1:200 to 1:800.

[Hydrothermal Synthesis of Zeolite]

The method by which the porous support having zeolite seed crystals adhered thereto is immersed in the aqueous sol is not specifically limited and may, for example, be a method in which the aqueous sol is loaded into a pressure-resistant vessel housing the porous support having zeolite seed crystals adhered thereto. Alternatively, a method in which the porous support having zeolite seed crystals adhered thereto is loaded into a pressure-resistant vessel housing the aqueous sol may be adopted. The pressure-resistant vessel that is used may be the same as any of those that can be used in production of the zeolite seed crystals.

When the porous separation layer is formed on the porous support by heating the aqueous sol in which the porous support having zeolite seed crystals adhered thereto is immersed and synthesizing a zeolite by hydrothermal synthesis, the heating temperature is preferably not lower than 100° C. and not higher than 250° C., and more preferably not lower than 150° C. and not higher than 200° C. Moreover, the heating time is preferably not less than 1 hour and not more than 50 hours. Particularly in a case in which the aqueous sol does not contain a boron source, the heating time is more preferably not less than 2 hours and not more than 20 hours. In a case in which the aqueous sol does contain a boron source, the heating time is more preferably not less than 12 hours and not more than 36 hours. Examples of methods by which the aqueous sol and the porous support in the pressure-resistant vessel can be heated include a method in which the pressure-resistant vessel is heated in a hot-air dryer and a method in which the pressure-resistant vessel is heated by a directly attached heater.

[Boil Washing]

A washing liquid used in boil washing of the separation membrane obtained through formation of the porous separation layer on the porous support may, for example, be distilled water. The boil washing time is preferably not less than 10 minutes and not more than 2 hours, and more preferably not less than 30 minutes and not more than 1.5 hours. Note that the boil washing may be repeated (for example, 2 or 3 times) and that the repetitions of the boil washing may each be carried out under the same boil washing conditions or different boil washing conditions. Moreover, drying treatment may be performed after the boil washing as necessary. The drying temperature of the separation membrane after the boil washing is preferably not lower than 70° C. and not higher than 100° C.

[Firing Treatment]

The separation membrane obtained through formation of the porous separation layer on the porous support is preferably subjected to firing treatment to remove the structure directing agent. The heating rate in the firing treatment is preferably not less than 0.1° C./minute and not more than 1° C./minute, and more preferably not less than 0.1° C./minute and not more than 0.5° C./minute. The firing temperature is preferably not lower than 400° C. and not higher than 800° C., and more preferably not lower than 400° C. and not higher than 600° C. Moreover, the cooling rate is preferably not less than 0.1° C./minute and not more than 1° C./minute, and more preferably not less than 0.1° C./minute and not more than 0.4° C./minute. The firing time (hold time) is preferably not less than 1 hour and not more than 30 hours, and more preferably not less than 5 hours and not more than 30 hours.

EXAMPLES

The following provides a more specific description of the present disclosure based on examples. However, the present disclosure is not limited to the following examples. In the following description, "%" and the like used to express quantities are by mass, unless otherwise specified.

In the examples and comparative examples, the following methods were used to measure and evaluate the average particle diameter of zeolite seed crystals, the average pore diameter and presence of acid sites in a porous support, the thickness of a porous separation layer, and the performance of a separation membrane.

<Average Particle Diameter of Zeolite Seed Crystals>

The particle diameters of 20 zeolite seed crystals were measured using a scanning electron microscope (SEM). The average value of the measured values was calculated and was taken to be the average particle diameter of the zeolite seed crystals.

<Average Pore Diameter of Porous Support>

The average pore diameter of a porous support was determined by mercury intrusion porosimetry using a mercury porosimeter (PoreMaster 60GT produced by Quantachrome Instruments). In measurement by mercury intrusion porosimetry using the mercury porosimeter, the pore diameter was determined by modeling pores as cylindrical shapes and using the Washburn equation: $-4\sigma \cos \theta = PD$ (in the Washburn equation, $\sigma$ represents the surface tension (N/m) of mercury, $\theta$ represents the contact angle (deg), D represents the pore diameter (m), and P represents the pressure (Pa)).

Moreover, in Examples 1 and 2 in which shirasu porous glass was used as a porous support, d10/d90 was calculated as the pore diameter distribution. Note that d10/d90 is a value obtained by dividing a pore diameter d10 at which cumulative pore volume is 10% of total pore volume by a pore diameter d90 at which cumulative pore volume is 90% of total pore volume.

<Presence of Acid Sites>

Ammonia temperature programmed desorption was carried out under the conditions shown below and acid content of a porous support was detected in a temperature range of higher than 450° C. and not higher than 600° C.

Pre-treatment: Vacuum degassing overnight at 200° C.

$NH_3$ adsorption: Adsorption of $NH_3$ at 50° C. and 1 kPa to 5 kPa

Desorption: Heating performed from 50° C. to 600° C. in 50° C. increments with pressure change measured at each temperature The amount of desorbed $NH_3$ was calculated from the change in pressure in order to confirm whether or not acid sites were present for the temperature range of higher than 450° C. and not higher than 600° C. More specifically, acid sites were judged to not be present (No) in a case in which the desorbed amount of $NH_3$ in the temperature range of higher than 450° C. and not higher than 600° C. was less than the detection limit (i.e., less than 0.4 μmol/g), and acid sites were judged to be present (Yes) in a case in which the desorbed amount of $NH_3$ in this temperature range was not less than the detection limit (i.e., 0.4 μmol/g or more).

<Thickness of Porous Separation Layer>

The thickness of a porous separation layer formed on a porous support was measured using a scanning electron microscope (SEM).

<Separation Performance>

[Separation Selectivity (Separation Factor) and Separation Efficiency (Permeation Flux)]

The results of a membrane separation test were used to calculate permeation flux F according to the following equation (I). Moreover, the separation factor α was calculated according to the following equation (II). The product of the separation factor α and the permeation flux F (i.e., F×α) was calculated, and separation performance was evaluated based on this value. A larger value for F×α indicates better separation performance.

$$F\ [kg/(m^2 \cdot h)] = W/(A \times t) \quad (I)$$

$$\alpha = (Y_n/Y_{bc})/(X_n/X_{bc}) \quad (II)$$

In equation (I), W is the mass [kg] of a component that has passed through the separation membrane, A is the effective area [m²] of the separation membrane, and t is processing time [h]. In equation (II), $X_n$ is the percentage content [mol %] of a linear hydrocarbon in a feedstock, $X_{bc}$ is the percentage content [mol %] of a branched hydrocarbon and a cyclic hydrocarbon in the feedstock, $Y_n$ is the percentage content [mol %] of the linear hydrocarbon in a permeate side sample, and $Y_{bc}$ is the percentage content [mol %] of the branched hydrocarbon and the cyclic hydrocarbon in the permeate side sample.

Note that in collection of the permeate side sample, the sampling time was set as 10 minutes as described below. Values for a point X minutes after the start of the test were calculated using samples collected with this point after X minutes as a central point in the sampling time of 10 minutes.

[Permeation Flux Maintenance Rate]

The results of the membrane separation test were used to calculate a maintenance rate for the permeation flux F. The maintenance rate of the permeation flux F was calculated as a ratio [%] of a value $F_{300}$ for the permeation flux [kg/m²/h] at a point 5 hours after the start of the test relative to a value $F_{10}$ for the permeation flux [kg/m$^2$/h] at a point 10 minutes after the start of the test, which was taken to be 100%.

Example 1

<Preparation of Aqueous Sol a for Seed Crystals>

A magnetic stirrer was used to mix 152.15 g of a tetrapropylammonium hydroxide aqueous solution of 22.5 mass % in concentration (produced by Tokyo Chemical Industry Co., Ltd.; 34.23 g in terms of tetrapropylammonium hydroxide as structure directing agent) and 48.44 g of ultrapure water. In addition, 99.41 g of tetraethoxysilane (produced by Sigma-Aldrich) was added as a silica source and was mixed therewith for 70 minutes at room temperature using the magnetic stirrer to yield an aqueous sol A for seed crystal preparation.

<Preparation of Zeolite Seed Crystals A>

The aqueous sol A for seed crystals was added into a stainless steel pressure-resistant vessel including a fluororesin inner cylinder, and then a reaction (hydrothermal synthesis) was carried out for 48 hours in a 130° C. hot-air dryer. Next, solid-liquid separation of the resultant reaction liquid was performed for 30 minutes by centrifugal separation in a centrifugal separator (4,000 rpm), and solid content was collected. The collected solid content was dried for 12 hours in an 80° C. thermostatic dryer, and then the dried solid was ground in a mortar to yield zeolite seed crystals A. It was confirmed that the resultant zeolite seed crystals A had an MFI-type structure by X-ray diffraction measurement. The zeolite seed crystals A had an average particle diameter of 500 nm.

<Adhesion of Zeolite Seed Crystals to Porous Support>

Shirasu porous glass (produced by SPG Technology Co., Ltd.; external diameter: 10 mm (±0.5 mm); thickness: 0.7 mm (±0.3 mm); average pore diameter: 1.5 μm; pore diameter distribution: 1.5 or less) serving as a circular tube-shaped porous support A was washed with acetone, subsequently dried, and then immersed in ultrapure water for 10 minutes. After this immersion in ultrapure water, 0.05 g of the zeolite seed crystals A obtained as described above were rubbed onto the outer surface of the wet porous support A and were dried for 12 hours in an 80° C. dryer to adhere the zeolite seed crystals A to the surface of the porous support A.

<Preparation of Aqueous Sol A for Porous Separation Layer>

A magnetic stirrer was used to mix 4.99 g of a tetrapropylammonium hydroxide aqueous solution of 22.5 mass % in concentration (produced by Tokyo Chemical Industry Co., Ltd.; 1.12 g in terms of tetrapropylammonium hydroxide as structure directing agent), 0.74 g of tetrapropylammonium bromide (produced by Wako Pure Chemical Industries, Ltd.) as a structure directing agent, 0.4 g of boric acid (produced by Wako Pure Chemical Industries, Ltd.) as a boron source, and 238.79 g of ultrapure water for 10 minutes at room temperature. In addition, 6.71 g of tetraethoxysilane (produced by Sigma-Aldrich) was added as a silica source and was mixed therewith for 60 minutes at room temperature using the magnetic stirrer to prepare an aqueous sol A for porous separation layer formation. The composition of the aqueous sol A, by molar ratio, was tetraethoxy silane:tetrapropylammonium hydroxide:tetrapropylammonium bromide:boric acid:water=1:0.2:0.1:0.2:419.

<Formation of Porous Separation Layer>

The aqueous sol A for a porous separation layer obtained as described above was added into a stainless steel pressure-resistant vessel. Next, the porous support A having the zeolite seed crystals A adhered thereto was immersed in the aqueous sol A for a porous separation layer, and a reaction (hydrothermal synthesis) was carried out for 24 hours in a 185° C. hot-air dryer to form a porous separation layer on the porous support. The porous support having the porous separation layer formed thereon was subjected to two repetitions of boil washing for 1 hour using distilled water as a washing liquid. Thereafter, the porous support having the porous separation layer formed thereon was dried for 12 hours using an 80° C. thermostatic dryer. Next, firing was performed to remove the structure directing agents (tetrapropylammonium hydroxide and tetrapropylammonium bromide) contained in the porous separation layer, and thereby obtain a separation membrane. The firing conditions were as follows.

Heating rate: 0.25° C./minute
Firing temperature: 500° C.
Firing time (hold time): 20 hours
Cooling rate: 0.38° C./minute The thickness of the porous separation layer in the resultant separation membrane was measured. Moreover, X-ray diffraction measurement of the porous separation layer was performed to obtain an X-ray diffraction pattern. As a result, it was confirmed that the porous separation layer contained an MFI-type zeolite based on the obtained X-ray diffraction pattern.

<Membrane Separation Test>

The separation membrane obtained as described above was subjected to a membrane separation test using a test apparatus 1 illustrated in FIG. 1.

[Test Apparatus]

The test apparatus 1 illustrated in FIG. 1 includes a feedstock tank 2, a liquid feed pump 3, a first heat exchanger 4, a separator 5, and a second heat exchanger 7. The separator 5 is configured by setting up the separation membrane obtained as described above in a circular tube. The test apparatus 1 illustrated in FIG. 1 also includes a cold trap 6 and a sampling cold trap 13 that are connected to the separator 5 via a three-way valve 10, and a vacuum pump 11 that is connected downstream of the cold trap 6 and the cold trap 13 via a three-way valve 14. Moreover, the test apparatus 1 includes a sampling valve 12 between the feedstock tank 2 and the liquid feed pump 3, and a back pressure valve 8 and a pressure gauge 9 downstream of the separator 5.

In the test apparatus 1 illustrated in FIG. 1, a feedstock loaded into the feedstock tank 2 is fed to the first heat exchanger 4 by the liquid feed pump 3 and is heated to a temperature at least as high as the temperature at which the feedstock vaporizes. The vaporized feedstock is fed to the separator 5 as a gas phase and then undergoes separation (membrane separation) of components by the separator 5 including the separation membrane. In the test apparatus 1, the vacuum pump 11 is used to maintain a reduced pressure state at the permeate side of the separation membrane. A permeate that has passed through the separation membrane is fed to the connected cold trap 6 or sampling cold trap 13 via the three-way valve 10. On the other hand, a retentate that has not passed through the separation membrane in the separator 5 is condensed through cooling by the second heat exchanger 7 and is returned to the feedstock tank 2. Note that back pressure in the test apparatus 1 is adjusted by the back pressure valve 8 and the pressure gauge 9 provided downstream of the separator 5. In the test apparatus 1, a permeate that has passed through the separation membrane in the separator 5 can be extracted as a permeate side sample through switching of the three-way valves 10 and 14.

[Membrane Separation]

The membrane separation test was implemented as follows using the test apparatus 1 illustrated in FIG. 1.

Specifically, a C5 hydrocarbon mixture (C5 fraction) containing linear, branched, and cyclic hydrocarbons having a carbon number of 5 was first loaded into the feedstock tank 2 and a degassing operation was performed three times. Thereafter, a feedstock circulation process was initiated in which the hydrocarbon mixture was fed to the separator 5 by the liquid feed pump 3, via the first heat exchanger 4 heated to 70° C. so as to be fed as a gas phase, and was then condensed by the second heat exchanger 7 and returned to the feedstock tank 2. After the feedstock circulation process had been initiated, operation was continued until the temperature of the system reached a steady state. Once the temperature of the system reached a steady state, the back pressure valve 8 was used to increase the pressure at the retentate side to 150 kPa and the vacuum pump 11 was operated to reduce the pressure at the permeate side (cold trap 6 and cold trap 13) to −100 kPa. After a stable temperature and pressure had been confirmed in the system, the three-way valve 10 at the permeate side was opened to start the membrane separation test. In other words, the membrane separation test was performed at a temperature of 70° C. and with a pressure difference between the retentate side and the permeate side of 250 kPa.

Extraction of a sample at the permeate side was started after 5 minutes had passed from the start of the membrane separation test. Specifically, the three-way valves 10 and 14 were used to switch the flow path at the permeate side from the cold trap 6 to the sampling cold trap 13, and a permeate side sample was extracted by collection as a condensate in the sampling cold trap 13. The sampling time during this was set as 10 minutes. The permeate side sample (condensate) was weighed and was measured by a gas chromatograph to determine the molar ratio of a linear component with a branched component and a cyclic component. These measurement results were used to evaluate performance of the separation membrane at a point 10 minutes after the start of the membrane separation test. The results are shown in Table 1.

A sample was also taken 5 hours after the start of the membrane separation test by the same procedure as described above. Moreover, performance of the separation membrane at a point 5 hours after the start of the membrane separation test was evaluated in the same manner as described above. The results are shown in Table 1.

Example 2

A separation membrane was prepared and evaluated in the same way as in Example 1 with the exception that an aqueous sol B for a porous separation layer that was prepared without compounding of boric acid as a boron source was used instead of the aqueous sol A for a porous separation layer, and the reaction (hydrothermal synthesis) time in the 185° C. hot-air dryer after immersion in the aqueous sol B for a porous separation layer in the porous separation layer formation step was changed to 14 hours. The results are shown in Table 1. It was confirmed that the porous separation layer of the separation membrane contained an MFI-type zeolite as a result of X-ray diffraction measurement of the porous separation layer.

Comparative Example 1

A separation membrane was prepared and evaluated in the same way as in Example 1 with the exception that a porous support B made of mullite (product name: PM Tube; produced by Nikkato Corporation; external diameter: 12 mm; internal diameter: 9 mm; length: 100 mm; average pore diameter: 1.4 µm) was used instead of the porous support A. The results are shown in Table 1. It was confirmed that the porous separation layer of the separation membrane contained an MFI-type zeolite as a result of X-ray diffraction measurement of the porous separation layer.

Comparative Example 2

A separation membrane was prepared and evaluated in the same way as in Example 2 with the exception that a porous support B made of mullite (product name: PM Tube; produced by Nikkato Corporation; external diameter: 12 mm; internal diameter: 9 mm; length: 100 mm; average pore diameter: 1.4 µm) was used instead of the porous support A. The results are shown in Table 1. It was confirmed that the porous separation layer of the separation membrane contained an MFI-type zeolite as a result of X-ray diffraction measurement of the porous separation layer.

TABLE 1

| | | Example 1 | Example 2 | Comparative Example 1 | Comparative Example 2 |
|---|---|---|---|---|---|
| Seed crystals | Average particle diameter [nm] | 500 | 500 | 500 | 500 |
| Porous support | Type | Shirasu porous glass | Shirasu porous glass | Mullite | Mullite |
| | Average pore diameter [µm] | 1.5 | 1.5 | 1.4 | 1.4 |
| | Acid sites | No | No | Yes | Yes |
| Porous separation layer | Type | MFI-type zeolite | MFI-type zeolite | MFI-type zeolite | MFI-type zeolite |
| | Inclusion of boron in aqueous sol | Yes | No | Yes | No |
| | Thickness [µm] | 60 | 40 | 60 | 40 |
| Separation performance | After 10 minutes Separation factor α [—] | 63.95 | 38.88 | 32.62 | 23.99 |
| | Permeation flux F [kg/(m$^2$ · h)] | 1.53 | 2.63 | 1.11 | 4.03 |
| | F × α [kg/(m$^2$ · h)] | 97.84 | 102.25 | 36.21 | 96.68 |
| | After 5 hours Separation factor α [—] | 74.03 | 40.64 | 33.41 | 16.29 |
| | Permeation flux F [kg/(m$^2$ · h)] | 0.99 | 1.81 | 0.26 | 0.58 |
| | F × α [kg/(m$^2$ · h)] | 73.29 | 73.56 | 8.69 | 9.45 |
| | Permeation flux maintenance rate [%] | 64.71 | 68.82 | 23.42 | 14.39 |

It can be seen from Table 1 that when membrane separation was performed using a separation membrane including a porous support for which acid content was not substantially detected by ammonia temperature programmed desorption in a temperature range of higher than 450° C. and not higher than 600° C. and a porous separation layer containing a zeolite that was disposed on the porous support, excellent separation performance could be maintained over a long period.

In particular, it can be seen that in Examples 1 and 2, the permeation flux maintenance rate was high (i.e., a good permeation flux was maintained even after 5 hours had passed from the start of the separation test) and the degree of deterioration of separation efficiency over time was remarkably low.

INDUSTRIAL APPLICABILITY

According to the present disclosure, it is possible to provide a separation membrane that can maintain excellent separation performance over a long period when used in membrane separation of a hydrocarbon mixture containing a linear hydrocarbon and a branched hydrocarbon and/or cyclic hydrocarbon of equivalent carbon number to the linear hydrocarbon.

REFERENCE SIGNS LIST 1 test apparatus
2 feedstock tank
3 liquid feed pump
4 first heat exchanger
5 separator
6 cold trap
7 second heat exchanger
8 back pressure valve
9 pressure gauge
10, 14 three-way valve
11 vacuum pump
12 sampling valve
13 sampling cold trap

The invention claimed is:

1. A separation membrane for use in membrane separation of a hydrocarbon mixture containing a linear hydrocarbon and either or both of a branched hydrocarbon and a cyclic hydrocarbon of equivalent carbon number to the linear hydrocarbon, the separation membrane comprising:
    a porous support consisting of shirasu porous glass, for which acid content is not substantially detected by ammonia temperature programmed desorption in a temperature range of higher than 450° C. and not higher than 600° C.; and
    a porous separation layer containing a zeolite that is disposed on the porous support.

2. The separation membrane according to claim 1, further comprising boron in at least one of the porous separation layer and the porous support.

3. A method of producing a separation membrane for use in membrane separation of a hydrocarbon mixture containing a linear hydrocarbon and either or both of a branched hydrocarbon and a cyclic hydrocarbon of equivalent carbon number to the linear hydrocarbon, the method comprising a step (A) of forming a porous separation layer containing a zeolite on a porous support for which acid content is not substantially detected by ammonia temperature programmed desorption in a temperature range of higher than 450° C. and not higher than 600° C., wherein the porous support is shirasu porous glass.

4. The method of producing a separation membrane according to claim 3, wherein the step (A) further includes immersing the porous support in an aqueous sol containing a silica source, a structure directing agent, and a boron source after one or more silicalite seed crystals have been adhered to the porous support.

5. The method of producing a separation membrane according to claim 4, wherein a ratio of an amount of the silica source and an amount of the boron source contained in the aqueous sol, as a molar ratio, is within a range of 1:0.01 to 1:1.

* * * * *